(12) United States Patent
Inou et al.

(10) Patent No.: US 8,489,252 B2
(45) Date of Patent: Jul. 16, 2013

(54) APPARATUS FOR CONTROLLING SPEED OF MOBILE OBJECT

(75) Inventors: Hiroshi Inou, Kariya (JP); Mamoru Sawada, Yokkaichi (JP); Seiji Totsuka, Tokai (JP)

(73) Assignee: Denso Corporation, Kariya (JP)

( * ) Notice: Subject to any disclaimer, the term of this patent is extended or adjusted under 35 U.S.C. 154(b) by 72 days.

(21) Appl. No.: 13/199,199

(22) Filed: Aug. 22, 2011

(65) Prior Publication Data
US 2012/0046803 A1    Feb. 23, 2012

(30) Foreign Application Priority Data

Aug. 23, 2010    (JP) .................................. 2010-186413

(51) Int. Cl.
*G05D 1/00*    (2006.01)
*G05D 3/00*    (2006.01)
*G06F 7/00*    (2006.01)

(52) U.S. Cl.
USPC ........ 701/1; 701/41; 701/42; 701/65; 701/93; 701/96; 701/300; 701/301; 701/514

(58) Field of Classification Search
USPC ............... 701/1, 41, 42, 93, 96, 65, 300, 301, 701/514; 382/104
See application file for complete search history.

(56) References Cited

U.S. PATENT DOCUMENTS

| 5,517,021 | A | * | 5/1996 | Kaufman et al. ............. 250/221 |
| 5,995,903 | A | * | 11/1999 | Smith et al. .................. 701/470 |
| 6,330,506 | B1 | | 12/2001 | Roulet |
| 7,519,459 | B2 | * | 4/2009 | Ito et al. .......................... 701/36 |
| 7,577,504 | B2 | * | 8/2009 | Sawada et al. .................. 701/38 |
| 7,616,782 | B2 | * | 11/2009 | Badawy ........................ 382/107 |
| 7,656,313 | B2 | * | 2/2010 | Victor et al. ............. 340/995.26 |
| 8,280,588 | B2 | * | 10/2012 | Inou et al. ...................... 701/41 |
| 2005/0200088 | A1 | * | 9/2005 | Sawada et al. ............. 280/5.507 |
| 2005/0209749 | A1 | * | 9/2005 | Ito et al. .......................... 701/36 |
| 2010/0036563 | A1 | * | 2/2010 | Inou et al. ...................... 701/41 |
| 2010/0049375 | A1 | * | 2/2010 | Tanimoto ......................... 701/1 |

FOREIGN PATENT DOCUMENTS

| JP | 5-270368 | 10/1993 |
| JP | 11-348696 | 12/1999 |
| JP | 2000-207699 | 7/2000 |
| JP | 2001-163082 | 6/2001 |
| JP | 2004-037220 | 2/2004 |
| JP | 2010-036777 | 2/2010 |

* cited by examiner

*Primary Examiner* — Khoi Tran
*Assistant Examiner* — Jorge Peche
(74) *Attorney, Agent, or Firm* — Harness, Dickey & Pierce, PLC

(57) ABSTRACT

In an obtainer for obtaining speed feeling of a driver of a movable object, a gaze point setter sets a gaze point of the driver, and a motion detector detects relative motion of an environmental field around the mobile object with respect to the mobile object. A divergent component calculator projects the relative motion of the environmental field in a coordinate system. The coordinate system is formed by modeling a retina sphere of the driver of the mobile object. The divergent calculator calculates each of divergent components of the projected relative motion of the environmental field radially expanding from the gaze point. A speed feeling calculator calculates speed feeling of the driver based on the divergent components of the projected relative motion of the environmental field radially expanding from the gaze point calculated by the divergent component calculator.

20 Claims, 8 Drawing Sheets

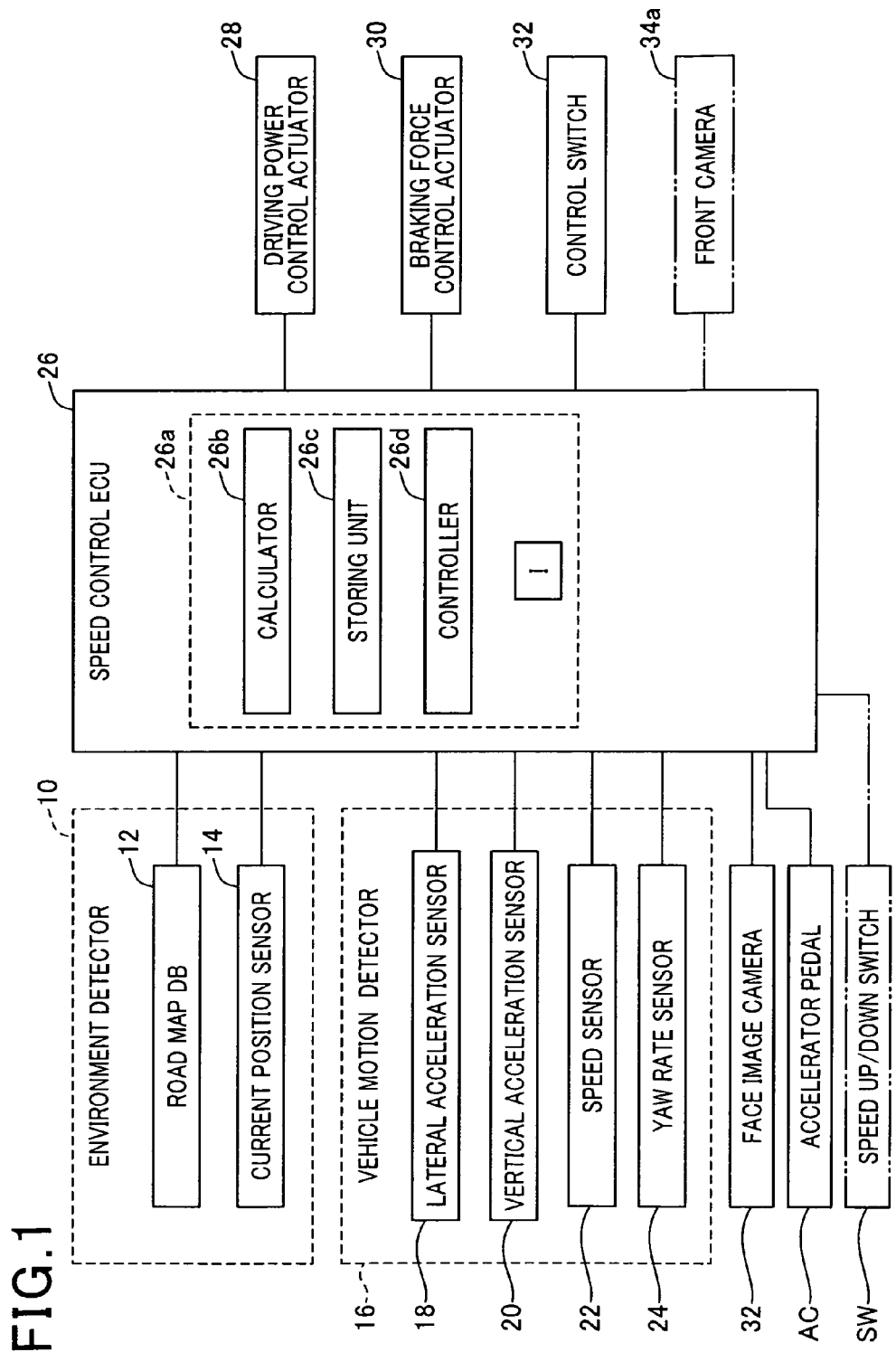

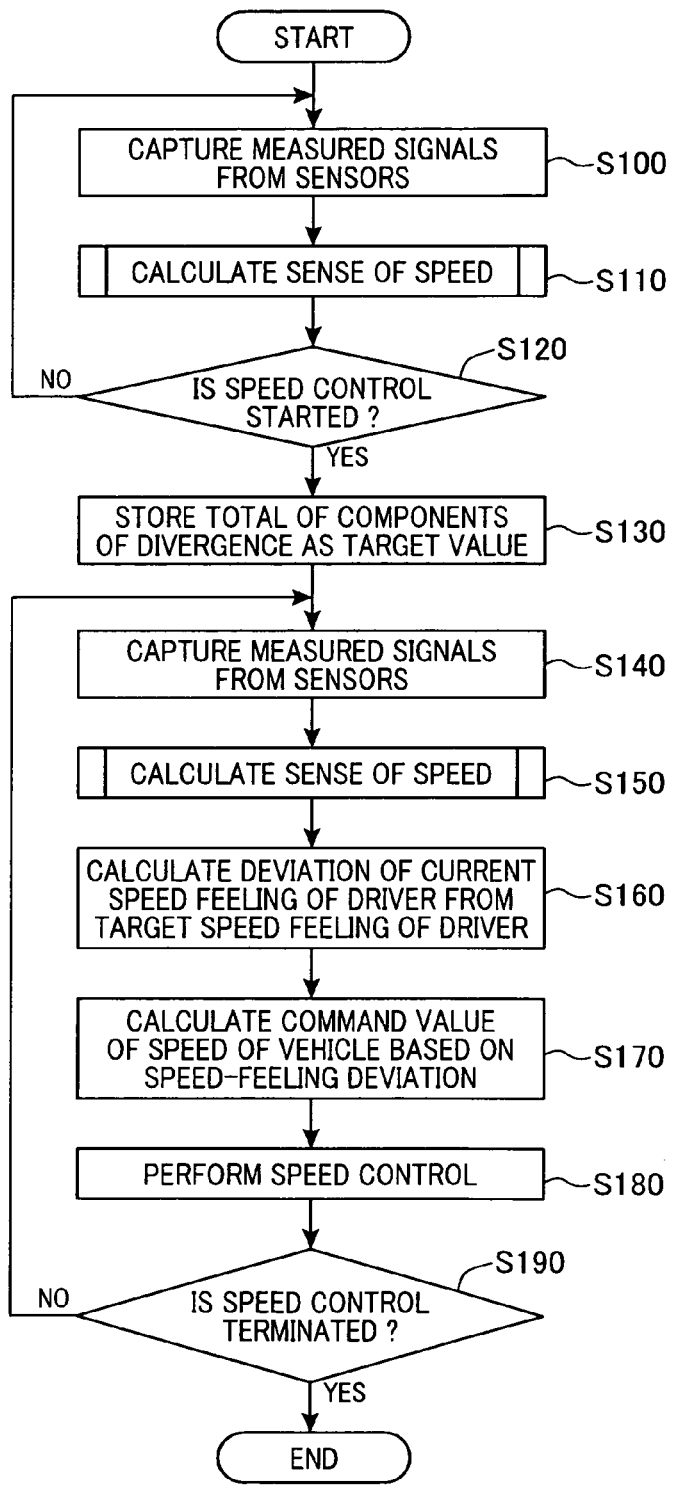

RUNNING ENVIRONMENTAL FIELD $\vec{n}$ : NORMAL VECTOR

APPARATUS FOR CONTROLLING SPEED OF MOBILE OBJECT

CROSS REFERENCE TO RELATED APPLICATIONS

This application is based on Japanese Patent Application 2010-186413 filed on Aug. 23, 2010. This application claims the benefit of priority from the Japanese Patent Application, so that the descriptions of which are all incorporated herein by reference.

TECHNICAL FIELD

The present disclosure relate to apparatuses for controlling the speed of a mobile object.

BACKGROUND

Japanese Patent Application Publication No. H05-270368 discloses a speed control system for controlling the speed of a vehicle to automatically keep the speed limit.

The speed control system includes a plurality of transceivers, a receiver, a speed detector, a comparator, and a brake controller. The plurality of transceivers are located on traffic lanes for vehicles. Each of the transceivers transmits a signal associated with the speed limit for vehicles. The receiver is installed in a vehicle to be controlled, and receives the signal transmitted from a transceiver to generate a first signal associated with the speed limit. The speed detector generates a second signal associated with the speed of the controlled vehicle that is running. The comparator compares the first signal with the second signal, and the brake controller receives the result of the comparison, and gives a third signal to the brakes of the controlled vehicle. Specifically, if the speed of the running controlled vehicle is higher than the speed limit, the brake controller actuates the brakes to reduce the speed of the controlled vehicle to be equal to or lower than the speed limit.

SUMMARY OF THE INVENTION

The inventors have discovered that there is a point to be solved in the aforementioned patent publication.

Specifically, the speed control system disclosed in the patent publication controls the speed of a vehicle to be controlled based on the speed limit established by regulation. For this reason, the speed control system disclosed in the aforementioned patent publication controls the speed of the controlled vehicle to be equal to or lower than the speed limit without any consideration of the shape of a road on which the controlled vehicle is travelling, such as a straight or curve.

However, if the controlled vehicle runs on a curve road at the same speed as that on a straight road, occupants of the controlled vehicle may feel that the speed of the controlled vehicle is too fast. This may result in that the occupants feel uncomfortable and/or fear. In the related arts, because it is difficult to grasp speed feeling of the driver as a specific value, it is difficult to control the speed feeling of the driver.

In view of the circumstances set forth above, one aspect of the present disclosure seeks to provide obtainers for obtaining speed feeling of a driver of a mobile object as a specific value.

An alternative aspect of the present disclosure seeks to provide apparatuses for controlling a speed of a mobile object, which are designed to address such a requirement set forth above.

Specifically, a further aspect of the present disclosure aims to provide such apparatuses for reducing an occupant of the mobile object from feeling uncomfortable or fear in controlling a speed of the mobile object.

The inventors of the present disclosure have focused that, while a mobile object is moving, a driver of the mobile object is visually aware of the motion of the mobile object by visually recognizing the flow of the environmental field around the mobile object. The flow of the environmental field visually recognizable includes components of divergence (divergent components) radially expanding from a drier's gaze point, and components of curl (rotational components) rotated around the gaze point.

The inventors of the present disclosure have discovered that each component of divergence is tightly associated with the driver's sense of speed. That is, the components of divergence are increased with increase in the speed of the vehicle, and reduced with reduction in the speed of the vehicle. In addition, each component of divergence as one factor of the relative flow of the environmental field is characterized to increase with reduction in the distance with respect to the mobile object and to decrease with increase in the distance with respect to the mobile object.

If a vehicle as an example of the mobile object is turning, because rotational motion of the vehicle arises in addition to forward motion thereof, each component of divergence increases by the rotational motion of the vehicle as long as the speed of the turning vehicle is constant before turning. In addition, if the slope of the road surface on which the vehicle is traveling is changed, because vertical motion of the vehicle arises in addition to forward motion thereof, each component of divergence increases as long as the speed of the turning vehicle is constant before turning.

According to one aspect of the present invention based on the discovery, there is provided an obtainer for obtaining speed feeling of a driver of a movable object. The obtainer includes a gaze point setter that sets a gaze point of the driver of the mobile object, a motion detector that detects relative motion of an environmental field around the mobile object with respect to the mobile object, and a divergent component calculator. The divergent calculator projects the relative motion of the environmental field in a coordinate system. The coordinate system is formed by modeling a retina sphere of the driver of the mobile object. The divergent calculator calculates each of divergent components of the projected relative motion of the environmental field radially expanding from the gaze point. The obtainer includes a speed feeling calculator that calculates speed feeling of the driver based on the divergent components of the projected relative motion of the environmental field radially expanding from the gaze point calculated by the divergent component calculator.

The aspect of the present disclosure allows the speed feeling of the driver to be specifically grasped. This makes it possible to easily control the speed feeling of the driver to reduce the driver from feeling uncomfortable or fear due to the driver's speed feeling.

The above and/or other features, and/or advantages of various aspects of the present disclosure will be further appreciated in view of the following description in conjunction with the accompanying drawings. Various aspects of the present disclosure can include and/or exclude different features, and/or advantages where applicable. In addition, various aspects of the present disclosure can combine one or more feature of other embodiments where applicable. The descriptions of features, and/or advantages of particular embodiments should not be constructed as limiting other embodiments or the claims.

BRIEF DESCRIPTION OF THE DRAWINGS

Other aspects of the present disclosure will become apparent from the following description of an embodiment with reference to the accompanying drawings in which:

FIG. 1 is a block diagram of a speed control apparatus according to an embodiment of the present disclosure;

FIG. 2A is a flowchart schematically illustrating a drive support task to be executed by a speed control ECU illustrated in FIG. 1 according to the embodiment;

DETAILED DESCRIPTION OF EMBODIMENT

Figure 2B:
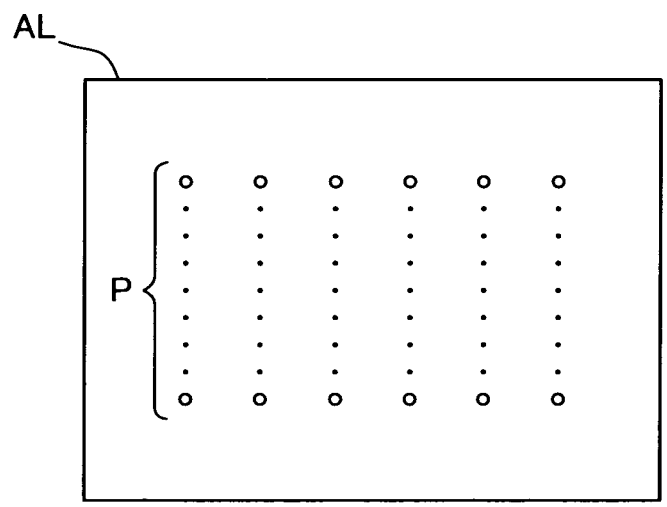
FIG. 2B is a view schematically illustrating a plurality of points set in a predetermined area in a running environmental field around a vehicle according to the embodiment.

An embodiment of the present invention will be described hereinafter with reference to the accompanying drawings.

An example of the structure of an apparatus AP for controlling the speed of a vehicle, such as a motor vehicle, which can run a road according to the present disclosure is illustrated in FIG. 1; this vehicle is an example of various mobile objects.

The apparatus AP installed in the vehicle includes an environment detector 10, a vehicle motion detector 16, a speed control ECU (Electronic Control Unit) 26, a driving power control actuator 28, a braking control actuator 30, a control switch 32, and a face image camera 34. Each of the elements 10, 16, 28, 30, 32, and 34 is communicably connected with the speed control ECU 26.

The environment detector 10 includes a road map database 12 and a current position sensor, such as a GPS receiver, 14. The road map database (DB) 12 stores therein data of road map. The current position sensor 14 is operative to determine a current position of the vehicle. The environment detector 10 is operative to detect a running environmental field, such as a running area, around the vehicle, based on the road map data stored in the road map database 12 and the current position of the vehicle determined by the current position sensor 14. For example, the environment detector 10 is operative to measure, as the running environmental field around the vehicle, the shape of a road running in the direction of forward movement of the vehicle from the current position. The environment detector 10 is also operative to send the detected running environment field around the vehicle to the speed control ECU 26.

The vehicle motion detector 16 includes a lateral acceleration sensor 18, a vertical acceleration sensor 20, a speed sensor 22, and a yaw rate sensor 24.

The lateral acceleration sensor 18 is operative to measure the magnitude of motion of the vehicle in the lateral direction (width direction) of the vehicle, and output a signal indicative of the measured magnitude of motion in the lateral direction of the vehicle to the speed control ECU 26.

The vertical acceleration sensor 20 is operative to measure the magnitude of motion of the vehicle in the vertical direction (height direction) of the vehicle, and output a signal indicative of the measured magnitude of motion in the vertical direction of the vehicle to the speed control ECU 26.

The speed sensor 22 is operative to measure the speed of the vehicle, and output a signal indicative of the measured speed of the vehicle to the speed control ECU 26.

The yaw rate sensor 24 is operative to measure the yaw rate of the vehicle, and output a signal indicative of the measured yaw rate of the vehicle to the speed control ECU 26; the yaw rate is a rate of change in a turning angle of the vehicle in its turning direction.

The control switch 32 is designed to be operable by the driver. When turned ON by the driver, the control switch 32 sends, to the speed control ECU 26, a trigger signal to start a drive support task.

The face image camera 34 is operative to successively pick up face images of a driver of the vehicle, and successively output, to the speed control ECU 26, the face images successively picked thereby.

The speed control ECU 26 is designed as, for example, a normal microcomputer circuit consisting of, for example, a CPU, a storage medium 26a including a ROM (Read Only Memory), such as a rewritable ROM, a RAM (Random Access Memory), and the like, an IO (Input and output) interface, and so on. The normal microcomputer circuit is defined in this embodiment to include at least a CPU and a main memory therefor.

The storage medium 26a stores therein beforehand various programs.

The speed control ECU 26 includes, as functional modules, a calculator 26b, a storing unit 26c, and a controller 26d. These functional modules can be implemented by executing a speed control program P included in the various programs described later.

The calculator 26b is operative to calculate a parameter indicative of the driver's sense of speed based on the successively picked-up face images.

The storing unit 26c is operative to store, in the storage medium 26a, a value of the parameter calculated at the time when the driver instructs the speed control ECU 26 to start control the vehicle using the control switch 32; this value is stored in the storage medium 26a as a target value.

The controller 26d is operative to control the speed of the vehicle using the driving power control actuator 28 and the braking control actuator 30 such that a calculated value of the parameter is matched with the target value.

As the driving power control actuator 28, if a vehicle with an internal combustion engine (referred to simply as an engine) is used, each of a throttle valve for adjustment of intake airflow into the engine and an injector for adjusting a quantity of fuel to be sprayed into the engine can be used. If an electric vehicle, which uses an electric motor as a power source, is used, a controller for controlling electric power supplied from a battery to the electric motor to control the output of the electric motor can be used as the driving power control actuator 28.

As the braking force control actuator 30, a hydraulic pressure system employed in an ABS (Anti Lock Braking System) or a VSC (Vehicle Stability Control) system installed in the vehicle, which is designed to generate brake pressure to hydraulically apply, via a brake for each wheel, a braking force to a corresponding wheel to thereby slow down or stop the rotation of a corresponding wheel. As the braking force control actuator 30, a controller for controlling the gear position of the transmission of the vehicle to generate braking force. If the vehicle is an electric vehicle, an electric motor, which normally serves as a driver, serves as a generator that converts its kinetic energy into electrical energy during the vehicle decelerated can be used as the braking force control actuator 30.

Next, the speed control task to be executed by the speed control ECU 26 in accordance with the speed control program P will be described hereinafter with reference to FIG. 2A. For example, the speed control task is cyclically carried out by speed control ECU 26.

First, the speed control ECU 26 captures the measured signals outputted from the sensors 18, 20, 22, and 24, and captures the successively picked-up face images from the face image sensor 34 in step S100.

Next, the speed control ECU 26 calculates, based on the captured measured signals and the captured successive face images, the parameter indicative of the driver's sense of speed in step S110. The calculating process of the parameter indicative of the driver's sense of speed will be described hereinafter with reference to FIG. 3 as a subroutine of step S110.

Figure 3:
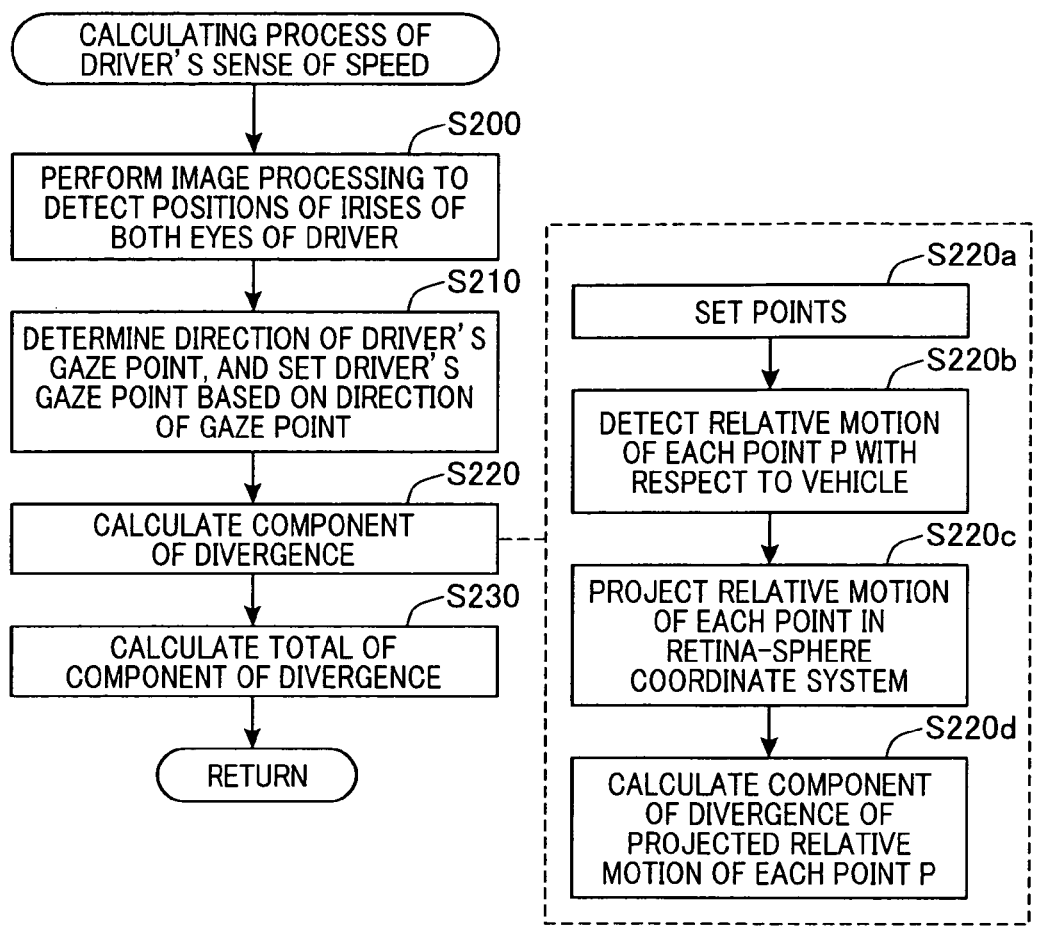
FIG. 3 is a flowchart schematically illustrating, as a subroutine, a calculating process of driver's sense of speed in step S110 of FIG. 2A.

Referring to FIG. 3, the speed control ECU 26 performs image processing of the successively picked-up face images to thereby detect the positions of the irises of both eyes of the driver based on the successively picked-up face images in step S200.

Subsequent to step S200, the speed control ECU 26 determines, based on the positions of the irises, the direction of a gaze point of the driver to which the driver's line of sight is directed in step S210.

In this embodiment, the environment detector 10 is equipped with the road map database 12 and the current position sensor 14. For this reason, in step S120, the speed control ECU 26 recognizes, based on the road map data stored in the road map database 12 and the current position of the vehicle determined by the current position sensor 14, the running environmental field around the vehicle, such as the shape of a road running in the direction of forward travel of the vehicle from the current position. Then, in step S210, the speed control ECU 26 sets, in the recognized running environmental field around the vehicle, the gaze point of the driver based on the determined direction of the gaze point of the driver to which the driver's line of sight is directed.

Following step S210, the speed control ECU 26 performs a divergent-component (a component of divergence) calculating process in step S220. How to perform the divergent-component calculating process will be described in detail hereinafter.

First, the speed control ECU 26 sets a plurality of points P in a predetermined area AL, such as an area AL that the driver can visibly recognize, in the recognized running environmental field in step S220a. That is, the plurality of points P represents the recognized running environmental field around the vehicle. Preferably, the predetermined area AL can be set as an area on the road in front of the vehicle; this area is viewable by the driver through a windshield of the vehicle. This is because the driver of the vehicle gets speed feeling by viewing the environmental field in front of the vehicle through the windshield.

The shape formed by the arrangement of the plurality of points P can be a matrix pattern, a concentric pattern, a concentric ellipsoidal pattern, or the like. For example, FIG. 2B schematically illustrates a matrix pattern of the plurality of points P in the area AL in the running environmental field.

Note that the plurality of points P can be set such that a positional relationship between each point P and the vehicle is continuously constant, or they can be fixedly set in the running environment field such that a relative positional relationship between each point P and the vehicle varies with travel of the vehicle. If the plurality of points P are fixedly set in the running environment field such that a relative positional relationship between each point P and the vehicle varies with travel of the vehicle, when some points P at a near side of the vehicle disappear from the area AL, corresponding points P are newly set at a far side of the vehicle. This maintains the number of points P constant irrespective of travel of the vehicle.

Subsequent to step S220a, the speed control ECU 26 detects, based on the measured signals of the lateral acceleration sensor 18, vertical acceleration sensor 20, speed sensor 22, and yaw rate sensor 24, motion of the vehicle in step S220b. Then, in step S220b, the speed control ECU 26 converts the detected motion of the vehicle into relative motion of the running environmental field with respect to the vehicle, that is, converts the detected motion of the vehicle into relative motion of each point P with respect to the vehicle, thus detecting the relative motion of each point P with respect to the vehicle. That is, because the flow (motion) of the running environmental field (road) visibly recognized by the driver results from relative motion between the driver and the running environmental field, it is possible to detect the relative motion of each point P with respect to the vehicle based on the motion of the vehicle.

Following step S220b, the speed control ECU 26 projects the relative motion of each point P in a three-dimensional coordinate system formed by modeling a retina sphere of the driver of the vehicle assuming that the driver observes the gaze point closely in step S220c; the three-dimensional coordinate system will be referred to as a "retina-sphere coordinate system".

Then, the speed control ECU 26 calculates a component of divergence of the projected relative motion of each point P; the component of divergence of the projected relative motion of each point P represents a divergent component of the projected relative motion of a corresponding point P radially expanding from the gaze point in step S220d. That is, the speed control ECU 26 calculates divergent components in the relative flow of the environmental field visually recognized by the driver; each of the divergent components of the relative flow of the environmental field relatively diverges radially from the gaze point with respect to the driver in step S220d.

Figure 4A:
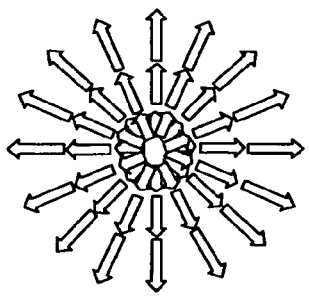
FIG. 4A is a view schematically illustrating components of divergence radially expanding from a gaze point according to the embodiment.
Figure 4B:
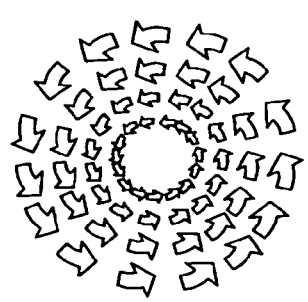
FIG. 4B is a view schematically illustrating components of curl rotated around the gaze point according to the embodiment.

Specifically, while the vehicle is running, the driver of the vehicle is visually aware of the motion of the vehicle by visually recognizing the flow of the environmental field around the vehicle. The flow of the environmental field visually recognizable includes components of divergence (divergent components) radially expanding from the gaze point (see FIG. 4A), and components of curl (rotational components) rotated around the gaze point (see FIG. 4B).

The components of divergence are increased with increase in the speed of the vehicle, and reduced with reduction in the speed of the vehicle. Thus, each component of divergence is tightly associated with the driver's sense of speed.

Each component of divergence as one factor of the relative flow of the environmental field is characterized to increase with reduction in the distance with respect to the vehicle and to decrease with increase in the distance with respect to the vehicle. If the vehicle is turning, because rotational motion of the vehicle arises in addition to forward motion thereof, each component of divergence of the projected relative motion of each point P increases by the rotational motion of the vehicle as long as the speed of the turning vehicle is constant before turning. In addition, if the slope of the road surface on which the vehicle is traveling is changed, because vertical motion of the vehicle arises in addition to forward motion thereof, each component of divergence of the projected relative motion of each point P increases as long as the speed of the turning vehicle is constant before turning.

In step S220d, the speed control ECU 26 calculates the component of divergence of each point P using the following procedure.

Figure 5A:
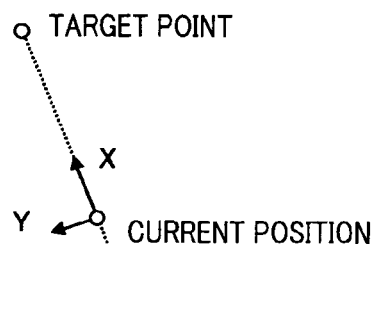
FIG. 5A is a view schematically illustrating a relationship between an X axis and a Y axis of an orthogonal coordinate system set by the speed control ECU according to the embodiment.
Figure 5B:
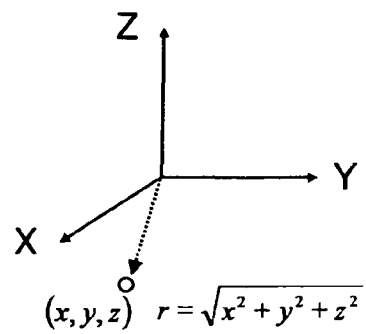
FIG. 5B is a view schematically illustrating the orthogonal coordinate system set by the speed control ECU according to the embodiment.

First, the speed control ECU 26 defines, in the storage medium 26a, an orthogonal coordinate system by setting: the gaze point to a target point, a direction from the current position of the vehicle (the driver's eye-point position) toward the target point to the X axis, a direction orthogonal to the X axis and extending in the lateral direction of the vehicle to the Y axis, and a direction orthogonal to the X and Y axes and extending in the vertical direction of the vehicle to the Z axis (see FIG. 5A). Next, as illustrated in FIG. 5B, the speed control ECU 26 obtains coordinates (x, y, z) of the plurality of points P.

Figure 5C:
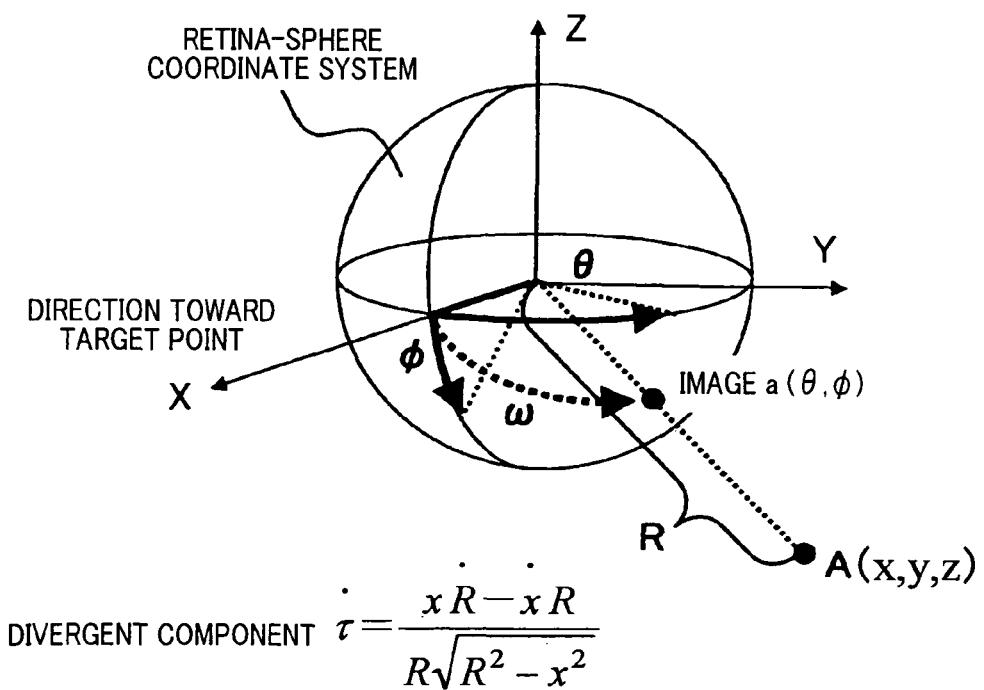
FIG. 5C is a view schematically illustrating a relationship between the orthogonal coordinate system and a retinasphere coordinate system defined by the speed control ECU according to the embodiment.

As illustrated in FIG. 5C, the relative motion of a point A with a coordinate (x, y, z) at a distance R from the origin of the orthogonal coordinate system is projected in the retina-sphere coordinate system (see step S220c). Note that the point A in the orthogonal coordinate system is converted into a point (an image) a (θ, φ) in the retina-sphere coordinate system; θ represents the azimuth angle from the X axis on the XY plane formed by the X axis and Y axis, and φ represents the elevation angle from the X axis on the XZ plane formed by the X axis and the Z axis.

Then, the speed control ECU 26 calculates a component t of divergence of the projected relative motion of the point A in the retina-sphere coordinate system in the following equation [1]:

$$\dot{t} = \frac{x\dot{R} - \dot{x}R}{R\sqrt{R^2 - x^2}} \quad [1]$$

where dot (•) over a letter represents the time derivative 'd/dt (time).

That is, because the direction of the driver's line of sight to the gaze point is set as the X axis, a component of divergence radially extending from the gaze point can be calculated, based on the X-axis component of the vehicle speed, the R-directional component of the vehicle speed, a corresponding point of three-dimensional coordinates (x, y, z), and the distance R. The R-directional component of the vehicle speed can be obtained by combining a component of the vehicle speed in the front and back direction of the vehicle, a component of the vehicle speed in the lateral direction of the vehicle, and a component of the vehicle speed in the vertical direction of the vehicle speed. The component of the vehicle speed in the front and back direction of the vehicle can be obtained based on the measured signal outputted from the vehicle speed sensor 22, the component of the vehicle speed in the lateral direction of the vehicle can be obtained by the measured signal outputted from the lateral acceleration sensor 18. Similarly, the component of the vehicle speed in the vertical direction of the vehicle can be obtained based on the measured signal outputted from the vertical acceleration sensor 20.

The speed control ECU 26 calculates the component of divergence of the projected relative motion of each point P in the same manner as the point A in step S220d.

After completion of the calculation of the component of divergence of the projected relative motion of each point P, the speed control ECU 26 proceeds to step S230, and determines, based on the calculated components of divergence of the projected relative motions of the respective points P, the parameter indicative of the driver's sense of speed in step S230.

Note that, when a vehicle travels (moves), the driver of the vehicle recognizes the motion of the vehicle based on the total flow of the environmental field in place of the flow of one point in the environmental field. Thus, the speed control ECU 26 according to this embodiment is programmed to calculate the total of the components of divergence of the projected relative motions of the respective points P as the parameter indicative of the driver's sense of speed in step S230. For example, in step S230, the speed control ECU 26 applies flux calculation in vector analysis (calculus) to obtain the total of the components of divergence of the projected relative motions of the respective points P.

Figure 6A:
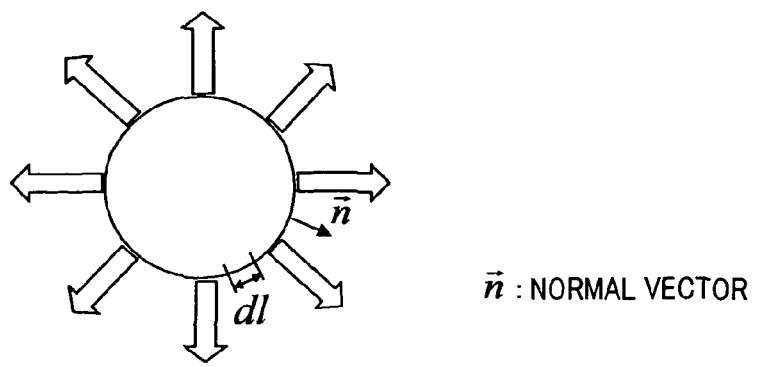
FIG. 6A is a view schematically illustrating a method to calculate the total of components of divergence according to the embodiment.
Figure 6B:
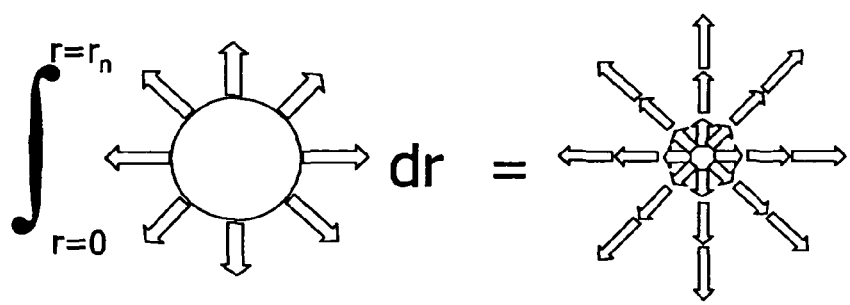
FIG. 6B is a view schematically illustrating a method to calculate the total of components of divergence according to the embodiment.

Specifically, as illustrated in FIG. 6A, the speed control ECU 26 establishes a closed loop about the gaze point in, for example, the storage medium 26a, and obtains flux out of the circular loop in accordance with the following equation [2]:

$$\text{Flux} = \oint \vec{f}_{div} \cdot \vec{n} \, dl \quad [2]$$

where l represents the closed loop, $\oint$ represents the closed line integral around the closed loop l, $\vec{f}_{div}$ represents a vector field in the closed loop l, $\vec{n}$ is a normal vector outward from the closed loop l, dl represents an infinitesimal element (a differential) of the closed loop l, and Flux represents divergence of the vector field across the closed loop l.

Next, in order to obtain the total of the components of divergence visibly recognized by the driver, the speed control ECU 26 calculates the integral of the Flux of a variable r of the radius on the internal from 0 to $r_n$ in accordance with the following equation [3] to thereby calculate the total of the components of divergence of the projected relative motions of the respective points P as the parameter indicative of the driver's sense of speed in step S230:

$$\text{Flux of Divergence} = \int_{r=0}^{r=r_n} \oint \vec{f}_{div} \cdot \vec{n} dl dr \qquad [3]$$

where $r_n$ represents a value of the variable r of the radius of the closed loop l that covers the predetermined area AL; 0 of the of the variable r of the radius of the closed loop l represents the gaze point.

As a result, it is possible to calculate the parameter indicative of the driver's sense of speed as the total of the components of divergence of the projected relative motions of the respective points P.

Figure 7:
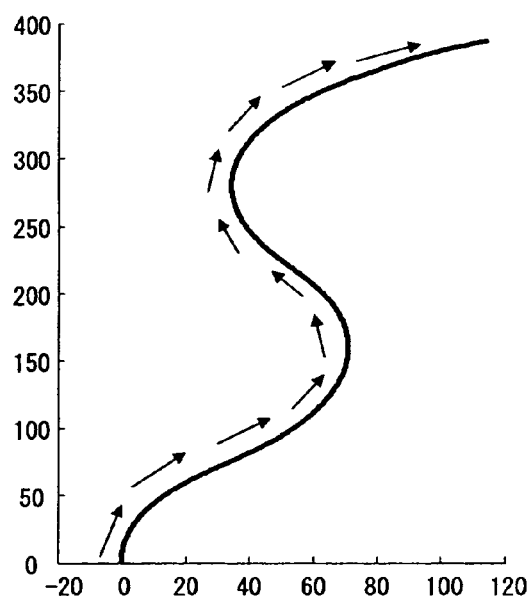
FIG. 7 is a view schematically illustrating a road with continuous curves in order to verify that the total of the components of divergence properly shows the driver's sense of speed according to the embodiment.

In order to verify that the total of the components of divergence properly shows the driver's sense of speed so that it is effective in control of the vehicle speed based on the total of the components of divergence, a skilled drove a vehicle in which the apparatus AP according to this embodiment is installed on a road with continuous curves illustrated in FIG. 7, and during the drive of the vehicle, the total (FOD) of the components of divergence was continuously calculated. Note that the road illustrated in FIG. 7 goes partly up and down.

Figure 8:
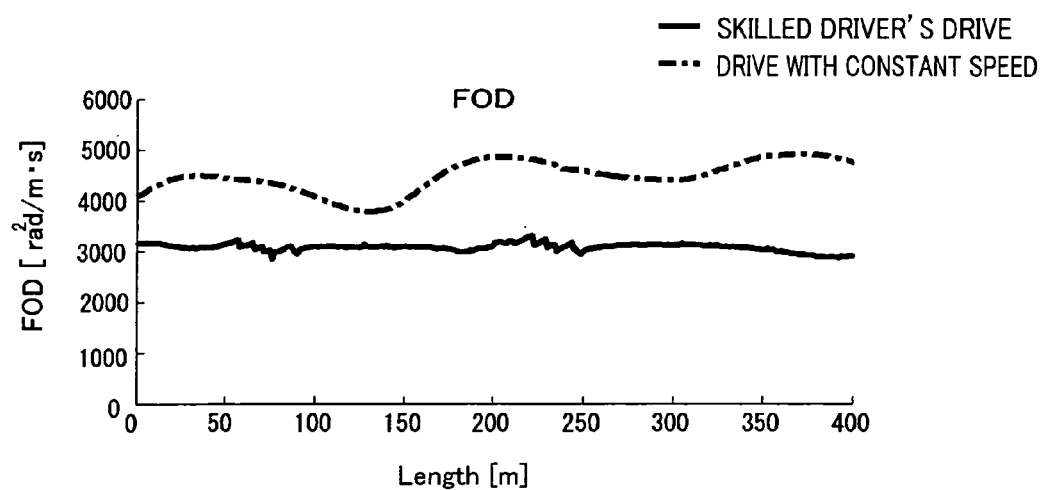
FIG. 8 is a graph schematically illustrating calculated values of the total (FOG) of the components of divergence during a skilled driver's drive of the vehicle as a solid line, and calculated values of the total of the components of divergence during the drive of the same vehicle on the same road with its speed being constant as alternate long and short dashed lines according to the embodiment.

FIG. 8 illustrates the calculated values of the FOG of the components of divergence as a graph illustrated as a solid line. In contrast, during the drive of the same vehicle on the same road with its speed being constant, the calculated value of the total (FOD) of the components of divergence was continuously calculated to be plotted as a graph illustrated as alternate long and short dashed lines.

FIG. 8 clearly demonstrates that the total (FOD) of the components of divergence when the vehicle was driven with its speed being constant fluctuates depending on the shape of the road, such as at the curves and/or up and down sections. This is because, as described above, if the vehicle travels at a curve of the road, because rotational motion of the vehicle arises in addition to forward motion thereof, each component of divergence of the projected relative motion of each point P increases by the rotational motion of the vehicle as long as the speed of the turning vehicle is constant before turning. In addition, if the slope of the road on which the vehicle is traveling is changed, because vertical motion of the vehicle arises in addition to forward motion thereof, each component of divergence of the projected relative motion of each point P increases as long as the speed of the turning vehicle is constant before turning.

The sense of speed of any occupant, such as the driver and a passenger, during the drive of the vehicle with its speed being constant fluctuates with the same tendency of the fluctuations of the total (FOD) of the components of divergence.

In contrast, when the vehicle driven by the skilled driver was travelled at each curve or at each up and down portion of the same road, although the speed of the vehicle was decelerated, the total (FOD) of the components of divergence is substantially constant independently of the shape of the road. At that time, the sense of speed of any occupant, such as the driver and a passenger, during the drive of the vehicle by the skilled person is also substantially constant.

These results of the verification demonstrate that the total (FOD) of the components of divergence properly shows the driver's sense of speed, and such a skilled driver is expected to drive the vehicle with the total of the components of divergence, in other words, the driver's sense of speed being automatically constant.

For this reason, the speed control ECU 26 according to this embodiment is configured to control the speed of the vehicle such that the total of the components of divergence is kept constant. This allows even an unskilled driver to control the speed of the vehicle in the same manner as a skilled driver. During control of the speed of the vehicle, the driver's sense of speed is substantially kept constant irrespective of change of the shape of the road, making it possible to reduce each occupant of the vehicle from feeling uncomfortable or fear.

After completion of the operation in step S230, that is, after calculation of the parameter of the driver's sense of speed in step S110, the speed control ECU 26 returns to the main routine illustrated in FIG. 2A from the subroutine, and determines whether a speed-control start signal is sent from the control switch 32 by the driver's turn-on operation of the control switch 32 in step S120. Upon determining that the speed-control start signal is not sent from the control switch 32 (NO in step S120), the speed control ECU 26 returns to step S100, and repeats the operations in steps S100, S110, and S120 until the determination in step S120 is affirmative.

Thus, upon determining that the speed-control start signal is sent from the control switch 32 (YES in step S120), in step S130, the speed control ECU 26 stores, in the storage medium 26a, the total of the components of divergence as the parameter indicative of the driver's sense of speed calculated in step S110 as a target value of speed control (target speed feeling of the driver).

As described above, in the speed control task illustrated in FIG. 2A, the speed control ECU 26 repeatedly calculates the parameter indicative of the driver's sense of speed, and stores, in the storage medium 26a, the parameter indicative of the driver's sense of speed as the target value of speed control at the point of time when the control switch 32 is turned ON. This makes it possible to set the driver's sense of speed at the driver's turn-on of the control switch 32 as the target value of speed control. Note that the speed control ECU 26 can calculate the parameter indicative of the driver's sense of speed after turn-on of the control switch 32, and can store the calculated parameter in the storage medium 26a.

Subsequent to step S130, the speed control ECU 26 captures the measured signals outputted from the sensors 18, 20, 22, and 24, and captures the successively picked-up face images from the face image sensor 32 in the same procedure as step S100. Then, in step S150, the speed control ECU 26 calculates, based on the captured measured signals and the captured successive face images, the parameter indicative of the driver's sense of speed substantially in the same procedure as step S110 (steps S200 to S230). That is, in step S150, the speed control ECU 26 calculates the present parameter indicative of the driver's sense of speed at present. In step S150, in consideration of control delay, the speed control ECU 26 can calculate the parameter indicative of the driver's sense of speed at a future position of the vehicle after a lapse of N seconds since the present assuming that the speed of the vehicle is constant during the course of N seconds.

Following step S150, the speed control ECU 26 calculates the deviation of the parameter indicative of the driver's sense of speed at present (or at a future position of the vehicle after a lapse of N seconds since the present) from the target value of the parameter indicative of the driver's sense of speed in step S160. That is, in step S160, the speed control ECU 26 calculates the deviation of the current speed feeling of the driver from the target speed feeling of the driver. Then, the speed control ECU 26 calculates, based on the calculated parameter deviation (calculated speed-feeling deviation), a commanded value of the speed of the vehicle in step S170.

For example, the storage medium 26a stores therein information I designed as, for example, a map, a program, and/or a function; this information F represents a relationship between a variable of compensation for the commanded value of the speed of the vehicle and a variable of the parameter deviation. The information I can have been determined based on data obtained by tests and/or simulations using the apparatus AP and the vehicle or their equivalent computer models.

Specifically, speed control ECU 26 references the information I using a calculated value of the parameter deviation as a key to extract, based on a result of the reference, a value of the compensation for the commanded value of the speed of the vehicle corresponding to the calculated value of the parameter deviation in step S170.

Subsequent to step S170, the speed control ECU 26 compensates a currently set commanded value of the speed of the vehicle based on the value of the compensation, thus calculating a new commanded value of the speed of the vehicle in step S180. Thus, in step S180, the speed control ECU 26 performs control of the speed of the vehicle based on the calculated commanded value of the speed of the vehicle. For example, the speed control ECU 26 controls the driving power control actuator 28 and/or the braking control actuator 30 such that the current value of the speed of the vehicle is substantially matched with the calculated commanded value of the speed of the vehicle.

Next, the speed control ECU 26 determines whether the control switch 32 is turned OFF, in other words, no trigger signal is inputted from the control switch 32 in step S190. Until the determination of step S190 is affirmative (YES), the speed control ECU 26 cyclically performs the speed control task from step S140 to S190. When the determination of step S190 is affirmative (YES), the speed control ECU 26 terminates the speed control task.

As described above, a speed feeling obtainer (the calculator 26b) according to this embodiment is configured to calculate speed feeling of the driver based on the components of divergence of the projected relative motions of the respective points P. This configuration allows the speed feeling of the driver to be specifically grasped. This makes it possible to easily control the speed feeling of the driver to reduce the driver from feeling uncomfortable or fear due to the driver's speed feeling.

In addition, the speed control apparatus AP according to this embodiment is configured to calculate, as the parameter indicative of the driver's sense of speed, the total of the components of divergence of the projected relative motions of the respective points P, and control the speed of the vehicle such that the total of the components of divergence of the projected relative motions of the respective points P is substantially kept constant. This configuration allows even an unskilled driver to control the speed of the vehicle in the same manner as a skilled driver with the driver's sense of speed being substantially kept constant irrespective of change the shape of the road. Thus, it is possible to reduce the driver from feeling uncomfortable or fear.

The speed control apparatus AP according to this embodiment is adapted to automatically adjust the speed of the vehicle such that the driver gets feeling of constant speed without the driver's operation of an accelerator pedal AC.

In addition, the speed control apparatus AP can perform speed control of the vehicle during the driver's operation of the accelerator pedal AC. In this modification, the speed control apparatus AP can be configured to control the driving power control actuator 28 and/or the braking control actuator 30 such that the current value of the speed of the vehicle is substantially matched with any one of: the calculated commanded value of the speed of the vehicle, and a driver's desired value of the speed of the vehicle based on the operation of the accelerator pedal AC in step S180a. This modification controls the speed of the vehicle so that the controlled speed is equal to or lower than the commanded value of the speed of the vehicle obtained by the speed control apparatus AP as its upper limit, making it possible to improve the safety of vehicle speed control.

Like a conventional auto cruise system, the speed control apparatus AP can be provided with a speed-up/down switch SW (see FIG. 1 as illustrated by phantom lines). In response to a driver's operation of the speed-up/down switch SW, the controller 26d of the speed control ECU 26d increases/reduces the speed of the vehicle by, for example, a preset value. In this modification, the speed control apparatus AP can be configured to carry out the operations in steps S100 to S130 to update the total of the components of divergence as the target speed feeling of the driver each time the speed of the vehicle changes due to a driver's operation of the speed-up/down switch SW. This modification can control the speed of the vehicle such that the driver can get speed feeling corresponding to the controlled speed of the vehicle after the driver's operation of the speed-up/down switch SW.

The speed control ECU 26 according to this embodiment is configured to store, in the storage medium 26a, the total of the components of divergence of the projected relative motions of the respective points P as the target value of speed control in response to receiving an instruction to start speed control, but the present disclosure is not limited to the configuration. Specifically, the speed control ECU 26 can be configured to receive an instruction to start speed control only when the vehicle is going straight ahead on the road. This modification can control the speed of the vehicle such that, even if the vehicle is turning at a corner or the like, the driver's speed feeling is substantially matched with the driver's speed feeling (target speed feeling) obtained when the vehicle is going straight ahead on the road. This can more reduce the driver from feeling uncomfortable or fear even if the vehicle turns at a corner.

The present disclosure is not limited to the embodiment set forth above, and can be modified or deformed within the scope of the present disclosure.

In this embodiment, the speed control apparatus AP is equipped with the face image camera 34 to successively pick up face images of the driver of the vehicle, and the speed control apparatus AP is configured to detect the positions of the irises of both eyes of the driver based on the successively picked-up face images, and set, based on the positions of the irises, the gaze point of the driver. However, the present disclosure is not limited to the configuration.

Specifically, the speed control apparatus AP can be provided with a front camera 34a mounted on the vehicle (see phantom lines in FIG. 1), and can be configured to represent motion of each of a plurality of points set in an image picked up by the front camera as a vector, that is, an optical flow, and set, as the gaze point, one point with the minimum optical flow. This is because, based on psychological theories and other findings as wall as empirical knowledge, the driver is known to gaze at a point that least moves in the driver's sight. In this case, the speed control ECU 26 can calculate, in step S220b, the optical flow at each of the plurality of points, or can calculate the optical flows at some of the plurality of points; these points at which the optical flows are calculated are limited to be present on the road. One point with the minimum optical flow can be selected as the gaze point in some of the plurality of points; these points as candidate points of the gaze point are limited to be present on the road.

In step S210, the speed control ECU 26 can convert the detected motion of the vehicle by the vehicle motion detector 160 into relative motion of the running environmental field with respect to the vehicle, that is, can convert the detected motion of the vehicle into relative motion of each of a plurality of points P set in the predetermined area AL in the recognized running environmental field with respect to the vehicle, thus detecting the relative motion of each point P with respect to the vehicle. Based on the relative motion of each point P, the speed control ECU 26 can set, as the gaze point, one point with the minimum relative motion with respect to the vehicle.

In this modification, assuming that the driver of the vehicle views in the travel direction of the vehicle, the speed control ECU 26 can project the relative motion of each point P in the retina-sphere coordinate system formed by modeling the retina sphere of the driver of the vehicle. Then, the speed control ECU 26 calculates an amount of the projected relative motion of each point P; the amount of observed relative motion of each point P.

Figure 9:
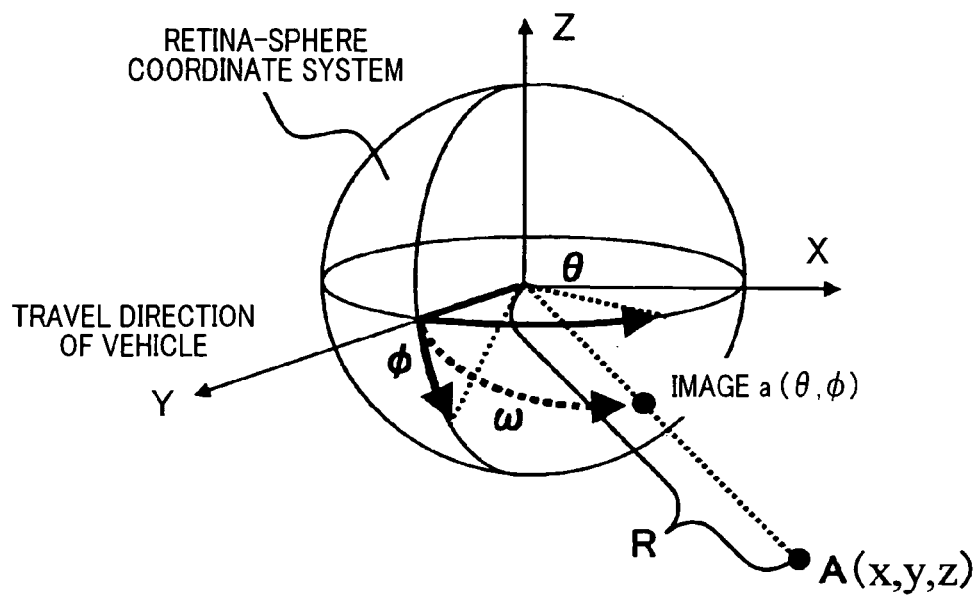
FIG. 9 is a view schematically illustrating a relationship between the orthogonal coordinate system and a retinasphere coordinate system defined by the speed control ECU according to the embodiment.

In FIG. 9 corresponding to FIG. 5C, an orthogonal coordinate system is defined by setting: the travel direction of the vehicle to the Y axis, a direction orthogonal to the Y axis and extending in the lateral direction of the vehicle to the X axis, and a direction orthogonal to the X and Y axes and extending in the vertical direction of the vehicle to the Z axis. Next, as illustrated in FIG. 9, the speed control ECU 26 obtains coordinates (x, y, z) of the plurality of points P.

As illustrated in FIG. 9, the relative motion of a point A with a coordinate (x, y, z) at a distance R from the origin of the orthogonal coordinate system is projected in the retina-sphere coordinate system. Note that the point A in the orthogonal coordinate system is converted into a point (an image) a ($\theta$, $\phi$) in the retina-sphere coordinate system; $\theta$ represents the azimuth angle from the X axis on the XY plane formed by the X axis and Y axis, and $\phi$ represents the elevation angle from the X axis on the X Z plane formed by the X axis and the Z axis.

That is, in step S210, the speed control ECU 26 calculates, as the observed motion, an absolute change rate of eccentric angle $\omega$ of the image a in accordance with the following equation [4]:

$$\dot{\omega} = \frac{V}{R}\sqrt{1 - \cos^2\theta \cdot \cos^2\phi} + \gamma \cdot \frac{\sin\theta \cdot \cos\phi}{\sqrt{1 - \cos^2\theta \cdot \cos^2\phi}} \quad [4]$$

where V represents the speed of the vehicle, and $\gamma$ represents the yaw rate.

The equation [4] is derived in the following manner. The eccentric angle $\omega$ is represented by using the azimuth angle $\theta$ and the elevation angle $\phi$ as shown in the following equation [5]:

$$\omega = \cos^{-1}(\cos\phi \cos\theta) \quad [5]$$

Figure 10:
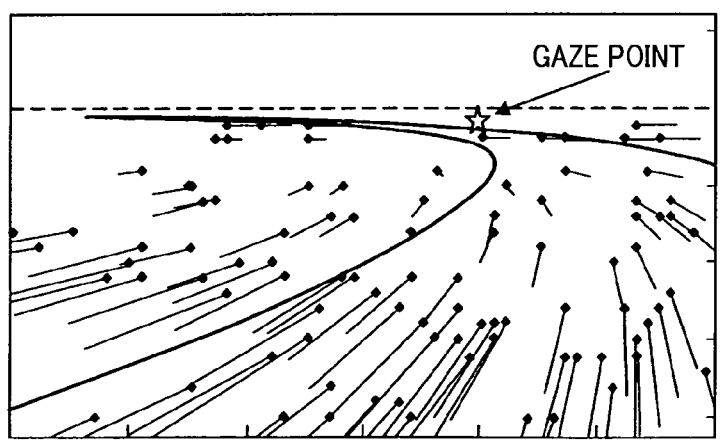
FIG. 10 is a view schematically illustrating a gaze point, and an absolute value of an eccentric-angle change rate of each of the plurality of points according to the embodiment.

In addition, the relationship between the angle $\theta$, the angle $\phi$, together with the eccentric w in the retina coordinate system and the coordinates (x, y, z) in the orthogonal coordinate system illustrated in FIG. 10 is represented by the following equations [6] to [10]:

$$\theta = \tan^{-1}\left(\frac{x}{y}\right) \quad [6]$$

$$\phi = \tan^{-1}\left(\frac{z}{\sqrt{x^2 + y^2}}\right) \quad [7]$$

$$x = y \cdot \tan\theta \quad [8]$$

$$y = R \cdot \cos\omega \quad [9]$$

$$z = \sqrt{x^2 + y^2} \cdot \tan\phi \quad [10]$$

Moreover, when the formula shown as the following equation [11] is employed to differentiate the equation [5], the following equation [12] is derived:

$$(\cos^{-1} x)' = \frac{1}{\sqrt{1 - x^2}} \quad [11]$$

$$\begin{aligned}\dot{\omega} &= \frac{1}{\sqrt{1 - (\cos\theta \cdot \cos\phi)^2}} \cdot (-\sin\theta \cdot \cos\phi \cdot \dot{\theta} - \cos\theta \cdot \sin\phi \cdot \dot{\phi}) \\ &= \frac{-(\sin\theta \cdot \cos\phi)}{\sqrt{1 - (\cos\theta \cdot \cos\phi)^2}} \cdot \dot{\theta} + \frac{-(\cos\theta \cdot \sin\phi)}{\sqrt{1 - (\cos\theta \cdot \cos\phi)^2}} \cdot \dot{\phi} \\ &= \alpha(\theta, \phi) \cdot \dot{\theta} + \beta(\theta, \phi) \cdot \dot{\phi}\end{aligned} \quad [12]$$

When the vehicle speed V and the yaw rate $\gamma$ are taken into consideration, the differentiated values of $\theta$ and $\phi$ are calculated, based on the equations [6] and [7], as the following equations [13] and [14]:

$$\begin{aligned}\dot{\phi} &= \frac{1}{1 + \left(\frac{z}{x^2 + y^2}\right)^2}\left(\frac{z}{\sqrt{z^2 + y^2}}\right)' \\ &= \frac{x^2 + y^2}{x^2 + y^2 + z^2}\left\{\frac{-z(x\dot{x} + y\dot{y}) + \dot{z}(x^2 + y^2)}{(x^2 + y^2)^{\frac{3}{2}}}\right\} \\ &= \frac{-zx\dot{x}}{(x^2 + y^2 + z^2)\sqrt{x^2 + y^2}} \\ &= -\frac{R\sin\phi \cdot R\cos\phi\cos\theta \cdot V}{R^2 R\cos\phi} \\ &= -\frac{V}{R}\cos\theta\sin\phi\end{aligned} \quad [13]$$

$$\begin{aligned}\dot{\theta} &= \frac{1}{1 + \left(\frac{x}{y}\right)^2}\left(\frac{x}{y}\right)' + \gamma = \frac{\dot{x}y - x\dot{y}}{x^2 + y^2} + \gamma \\ &= \frac{-VR\cos\phi \cdot \sin\theta}{R^2\cos^2\phi} + \gamma \\ &= \frac{-V\sin\theta}{R\cos\phi} + \gamma\end{aligned} \quad [14]$$

Substitution of the equations [13] and [14] into the equation [12] establishes the equation [4].

In step S210, the speed control ECU 26 can successively calculate, in accordance with the equation [4], the change rates of the respective points P using the positions ($\theta$, $\phi$), the distance R, the vehicle speed V, and the yaw rate $\gamma$. The change rate of each point P represents the amount of relative motion in the driver's visual sensation because it is calculated based on the retina-sphere coordinate system. That is, the speed control ECU 26 can convert physical relative motion of each point P set in the predetermined area AL into visual relative motion.

In step S210, the speed control ECU 26 sets the gaze point of the driver based on the change rate of the eccentric angle of each of the points P. Specifically, FIG. 10 schematically illustrates the absolute values of the eccentric-angle change rates of the respective points P, each of which is represented by a segment having a proportional length. As illustrated in FIG. 10, the speed control ECU 26 searches all of the absolute values of the eccentric-angle change rates for finding the minimum absolute value of a point P as the gaze point.

Note that, because the driver assumes to gaze at a point on the road while running the vehicle, a position of the gaze point can be limited on the road in front of the vehicle.

In the aforementioned embodiment, the speed control apparatus AP detects motion of the vehicle, and converts the detected motion of the vehicle into relative motion of the running environment field with respect to the vehicle, but the present disclosure is not limited thereto.

Specifically, the speed control apparatus AP can be configured to, using an object detecting unit, such as a millimeter laser, a laser radar, and a stereo camera, detect positional information, such as an azimuth direction and a distance from the vehicle, of at least one stationary object existing in the running environmental field, thus detecting motion of the at least one stationary object. As the at least one stationary object to be detected, a point on the road surface in front of the vehicle, a guardrail, a marker, or the like can be used. The speed control apparatus AP can detect relative motion of the at least one stationary object in the retina-sphere coordinate system based on the positional information of the at least one stationary object.

In the aforementioned embodiment, the speed control apparatus AP projects, in the retina-sphere coordinate system, the relative motion of each of the plurality of points P set in the area AL in the running environmental field, and calculates a component of curl of the projected relative motion of each point P, but the present disclosure is not limited thereto.

Specifically, because a target trajectory should be set on the road on which the vehicle is estimated to run, the plurality of points P can be set on the road on which the vehicle is estimated to run. This reduces processing load of the speed control ECU 26.

The speed control ECU 26 according to this embodiment is configured to store, in the storage medium 26a, the total of the components of divergence of the projected relative motions of the respective points P as the target value of speed control in response to receiving an instruction to start speed control, but the present disclosure is not limited to the configuration. Specifically, because each driver for the vehicle has a substantially unique sense of speed depending on his/her preference, the speed control ECU 26 can consider the speed feeling of each of individual drivers to be substantially constant.

Thus, for the first speed control of the vehicle for each of individual drivers, the speed control ECU 26 can store, in the storage medium 26a, the total of the components of divergence of the projected relative motions of the respective points P as the target value of speed control. For the next speed control of the vehicle and thereafter for a driver, the speed control ECU 26 can identify the driver, and carry out speed control based on the target value corresponding to the identified driver and stored in the storage medium 26a. How to identify any driver that is driving the vehicle can be to recognize the driver based on the successive face images of the corresponding driver, or to provide a plurality of switches for drivers and to identify any one of the drivers based on which switch is operated.

In the aforementioned embodiment, the vehicle is used as an example of mobile objects of the present disclosure. However, other types of mobile objects, such as an aircraft, a motorcycle, a wheelchair, and the like can also be used as the mobile object of the present disclosure.

While an illustrative embodiment of the present disclosure has been described herein, the present disclosure is not limited to the embodiment described herein, but includes any and all embodiments having modifications, omissions, combinations (e.g., of aspects across various embodiments), adaptations and/or alternations as would be appreciated by those in the art based on the present disclosure. The limitations in the claims are to be interpreted broadly based on the language employed in the claims and not limited to examples described in the present specification or during the prosecution of the application, which examples are to be constructed as non-exclusive.

What is claimed is:

1. A speed control apparatus comprising:
    a gaze point setter that sets a gaze point of a driver of a mobile object;
    a motion detector that detects motion of an environmental field around the mobile object with respect to the driver of the mobile object;
    a divergent component calculator that:
        projects the motion of the environmental field in a coordinate system, the coordinate system being formed by modeling a retina sphere of the driver of the mobile object, and
        calculates each of divergent components of the projected motion of the environmental field radially expanding from the gaze point;
    a total calculator that calculates a total of a number of the divergent components of the projected motion of the environmental field, the number of the divergent components being included in a predetermined area containing the gaze point; and
    a speed controller that controls the speed of the mobile object such that the total of the number of the divergent components of the projected motion of the environmental field is substantially kept constant.

2. The speed control apparatus according to claim 1, wherein the mobile object has a windshield, and the predetermined area is determined to correspond to the area of a windshield of the mobile object.

3. The speed control apparatus according to claim 2, wherein the motion detector comprises:
    a road map storing unit that stores therein a road map;
    a current position detector that detects a current position of the vehicle; and
    a vehicle-motion detector that detects motion of the vehicle in a lateral direction of the vehicle, and detects motion of the vehicle in a vertical direction of the vehicle,
    wherein the motion detector detects relative motion of each of the plurality of points with respect to the mobile object in a virtual running environmental field based on the detected motion of the vehicle in the lateral direction and the detected motion of the vehicle in the vertical direction, the virtual running environmental field being defined based on the road map and the detected current position of the vehicle.

4. The speed control apparatus according to claim 1, wherein the motion detector comprises an object detector that detects positions of objects existing in the environmental field around the mobile object as the environmental field, the motion detector detecting the motion of the environmental field with respect to the driver of the mobile object based on a detected position of a stationary object in the positions detected by the object detector.

5. The speed control apparatus according to claim 1, wherein the gaze point setter sets, as the gaze point, a point of the projected motion of the environmental field, when the motion of the environmental field detected by the motion detector is projected in the coordinate system formed by modeling the retina sphere of the driver of the mobile object, the projected motion of the environmental field being minimized at the point set as the gazes point.

6. The speed control apparatus according to claim 1, further comprising a driver camera that picks up an image of the driver, the image including an eye of the driver, wherein the gaze point setter analyzes the image including the eye of the driver picked up by the driver camera, thus setting the gaze point.

7. The speed control apparatus according to claim 1, further comprising a front camera that successively picks up images in a travelling direction of the vehicle, wherein the gaze point setter sets the gaze point based on optical flows in the picked-up images by the front camera.

8. The speed control apparatus according to claim 1, wherein the speed controller is configured to start control of the speed of the mobile object in response to when an instruction is inputted by the driver of the mobile object, set, as a target value, a value of the total of the number of the divergent components of the projected motion of the environmental field calculated by the total calculator when the instruction is inputted by the driver of the mobile object, and control the speed of the mobile object such that:
 a value of the total of the number of the divergent components of the projected motion of the environmental field calculated by the total calculator after calculation of the target value is substantially matched with the target value.

9. The speed control apparatus according to claim 8, wherein, after the start of control of the speed of the mobile object, the speed controller updates the target value according to when change of the speed of the mobile object is carried out by the driver.

10. The speed control apparatus according to claim 8, wherein, when a speed adjusting member for adjusting the speed of the mobile object is operated by the driver after the start of control of the speed of the mobile object, the speed controller adjusts the speed of the mobile object to be one of a value of the speed controlled by itself and a value of the speed based on the operation of the speed adjusting member.

11. The speed control apparatus according to claim 1, wherein the motion detector sets a plurality of points in the predetermined area, and detects motion of each of the plurality of points with respect to the mobile object with respect to the mobile object as the relative motion of the environmental field around the mobile object.

12. The speed control apparatus according to claim 11, wherein the mobile object has a windshield, and the predetermined area is determined to correspond to an area of the windshield of the mobile object.

13. The speed control apparatus according to claim 11, wherein the motion detector comprises:
 a road map storing unit that stores therein a road map;
 a current position detector that detects a current position of the vehicle; and
 a vehicle-motion detector that detects motion of the vehicle in a lateral direction of the vehicle, and detects motion of the vehicle in a vertical direction of the vehicle,
 wherein the motion detector detects relative motion of each of the plurality of points with respect to the mobile object in a virtual running environmental field based on the detected motion of the vehicle in the lateral direction and the detected motion of the vehicle in the vertical direction, the virtual running environmental field being defined based on the road map and the detected current position of the vehicle.

14. The speed control apparatus according to claim 11, wherein the motion detector comprises an object detector that detects positions of objects existing in the environmental field around the mobile object as the environmental field, the motion detector detecting the motion of the environmental field with respect to the driver of the mobile object based on a detected position of a stationary object in the positions detected by the object detector.

15. The speed control apparatus according to claim 11, wherein the gaze point setter sets, as the gaze point, a point of the projected motion of the environmental field, when the motion of the environmental field detected by the motion detector is projected in the coordinate system formed by modeling the retina sphere of the driver of the mobile object, the projected motion of the environmental field being minimized at the point set as the gazes point.

16. The speed control apparatus according to claim 11, further comprising a driver camera that picks up an image of the driver, the image including an eye of the driver, wherein the gaze point setter analyzes the image including the eye of the driver picked up by the driver camera, thus setting the gaze point.

17. The speed control apparatus according to claim 11, further comprising a front camera that successively picks up images in a travelling direction of the vehicle, wherein the gaze point setter sets the gaze point based on optical flows in the picked-up images by the front camera.

18. The speed control apparatus according to claim 11, wherein the speed controller is configured to start control of the speed of the mobile object in response to when an instruction is inputted by the driver of the mobile object, set, as a target value, a value of the total of the number of the divergent components of the projected motion of the environmental field calculated by the total calculator when the instruction is inputted by the driver of the mobile object, and control the speed of the mobile object such that:
 a value of the total of the number of the divergent components of the projected motion of the environmental field calculated by the total calculator after calculation of the target value is substantially matched with the target value.

19. The speed control apparatus according to claim 18, wherein, after the start of control of the speed of the mobile object, the speed controller updates the target value according to when change of the speed of the mobile object is carried out by the driver.

20. The speed control apparatus according to claim 18, wherein, when a speed adjusting member for adjusting the speed of the mobile object is operated by the driver after the start of control of the speed of the mobile object, the speed controller adjusts the speed of the mobile object to be one of a value of the speed controlled by itself and a value of the speed based on the operation of the speed adjusting member.

* * * * *